United States Patent
Thirumalai Rajan et al.

(10) Patent No.: US 10,301,302 B2
(45) Date of Patent: May 28, 2019

(54) CRYSTALLINE FORMS OF N-(2-CHLORO-6-METHY]PHENVN-2-[F6-[4-(2-HVDROXVETHVL)-L-PIPERAZIN-VIL-2-METHVIL-4-PVRIMIDINVLLAMINOL-5-THIAZOLECARBOXAMIDE AND THEIR PROCESS THEREOF

(71) Applicant: MSN LABORATORIES PRIVATE LIMITED, Hyderabad, Telangana (IN)

(72) Inventors: Srinivasan Thirumalai Rajan, Telangana (IN); Sajja Eswaraiah, Telangana (IN); Gutta Madhusudhan, Telangana (IN); Peri Seetha Rama Sarma, Telangana (IN); Mogal Khalil Ahamed, Telangana (IN)

(73) Assignee: MSN LABORATORIES PRIVATE LIMITED, Hyderabad, Telangana (IN)

( * ) Notice: Subject to any disclaimer, the term of this patent is extended or adjusted under 35 U.S.C. 154(b) by 0 days.

(21) Appl. No.: 15/741,086

(22) PCT Filed: Jun. 27, 2016

(86) PCT No.: PCT/IN2016/000167
§ 371 (c)(1),
(2) Date: Dec. 29, 2017

(87) PCT Pub. No.: WO2017/002131
PCT Pub. Date: Jan. 5, 2017

(65) Prior Publication Data
US 2018/0186784 A1    Jul. 5, 2018

(30) Foreign Application Priority Data

Jun. 29, 2015 (IN) ........................... 3281/CHE/2015
Apr. 22, 2016 (IN) ............................. 201641014060

(51) Int. Cl.
| | | |
|---|---|---|
| A61K 31/426 | (2006.01) | |
| A61K 31/496 | (2006.01) | |
| A61K 31/506 | (2006.01) | |
| C07D 417/14 | (2006.01) | |
| C07D 417/12 | (2006.01) | |
| B01D 9/00 | (2006.01) | |
| C07C 31/20 | (2006.01) | |

(52) U.S. Cl.
CPC ........... *C07D 417/14* (2013.01); *B01D 9/005* (2013.01); *C07C 31/205* (2013.01); *C07D 417/12* (2013.01); *C07B 2200/13* (2013.01)

(58) Field of Classification Search
CPC .. A61K 31/426; A61K 31/496; A61K 31/506; C07D 417/14
USPC ...................................... 514/252.14; 544/295
See application file for complete search history.

(56) References Cited

FOREIGN PATENT DOCUMENTS

| WO | WO 2005/077945 | 8/2005 |
| WO | WO 2010/139981 | 12/2010 |
| WO | WO 2014/086326 | 6/2014 |

OTHER PUBLICATIONS

International Search Report issued in International patent application No. PCT/IN2016/000167, dated Sep. 16, 2016.

*Primary Examiner* — Brenda L Coleman
(74) *Attorney, Agent, or Firm* — IP PUNDIT LLC

(57) ABSTRACT

The present invention relates to crystalline 1,2-Propanediol solvate of N-(2-chloro-6-methylphenyl)-2-[[6-[4-(2-hydroxyethyl)-1-piperazinyl]-2-methyl-4-pyrimidinyl]amino]-5-thiazolecarboxamide compound of formula-1b, its process for the preparation and its use in the preparation of anhydrous crystalline form (N-6) and monohydrate of N-(2-chloro-6-methylphenyl)-2-[[6-[4-(2-hydroxy ethyl)-1-piperazinyl]-2-methyl-4-pyrimidinyl]amino]-5-thiazolecarboxamide. [formula] 1,2-Propanediol solvate Formula-1b.

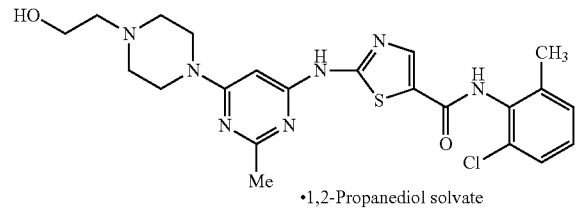

•1,2-Propanediol solvate

18 Claims, 5 Drawing Sheets

CRYSTALLINE FORMS OF N-(2-CHLORO-6-METHY]PHENVN-2-[F6-[4-(2-HVDROXVETHVL)-L-PIPERAZIN-VIL-2-METHVIL-4-PVRIMIDINVLLAMINOL-5-THIAZOLECARBOXAMIDE AND THEIR PROCESS THEREOF

RELATED APPLICATION

This application is a national phase application under 35 U.S.C. § 371 of International Application No. PCT/IN2016/000167, filed on Jun. 27, 2016, which claims priority to Indian Patent Application No. 3281/CHE/2015, filed on Jun. 29, 2015, and Indian Patent Application No. 201641014060, filed on Apr. 22, 2016; the disclosures of all of which are hereby incorporated by reference in their entirety.

FIELD OF THE INVENTION

The present invention relates to crystalline 1,2-Propanediol solvate of N-(2-chloro-6-methylphenyl)-2-[[6-[4-(2-hydroxyethyl)-1-piperazinyl]-2-methyl-4-pyrimidinyl]amino]-5-thiazolecarboxamide compound represented by the following structural formula-1b.

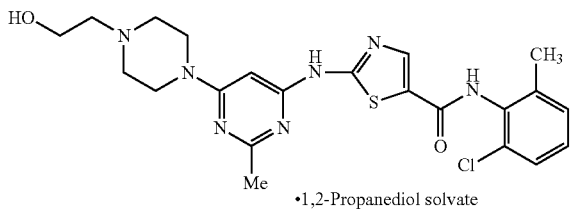 [SMILES: Cc1nc(Nc2ncc(C(=O)Nc3c(C)cccc3Cl)s2)cc(N2CCN(CCO)CC2)n1]

Formula-1b

•1,2-Propanediol solvate

The present invention also relates to improved processes for the preparation of anhydrous crystalline form (N-6) and monohydrate of N-(2-chloro-6-methylphenyl)-2-[[6-[4-(2-hydroxy ethyl)-1-piperazinyl]-2-methyl-4-pyrimidinyl]amino]-5-thiazolecarboxamide.

BACKGROUND OF THE INVENTION

N-(2-chloro-6-methylphenyl)-2-[[6-[4-(2-hydroxyethyl)-1-piperazinyl]-2-methyl-4-pyrimidinyl]amino]-5-thiazole carboxamide is generally known as Dasatinib and is represented by the following structural formula-1.

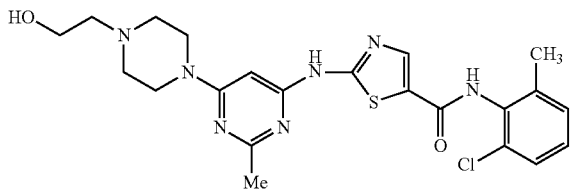

Formula-1

Dasatinib is a cyclic protein tyrosine kinase inhibitor indicated for newly diagnosed adults with Philadelphia chromosome-positive (Ph+) chronic myeloid leukemia (CML) in chronic phase; adults with chronic, accelerated, or myeloid or lymphoid blast phase Ph+ CML with resistance or intolerance to prior therapy including imatinib; and, adults with Philadelphia chromosome-positive acute lymphoblastic leukemia (Ph+ ALL) with resistance or intolerance to prior therapy. It is also being evaluated for use in numerous other cancers, including advanced prostate cancer.

Dasatinib is approved in USFDA as SPRYCEL™ and is chemically mentioned in the label as N-(2-chloro-6-methylphenyl)-2-[[6-[4-(2-hydroxyethyl)-1-piperazinyl]-2-methyl-4-pyrimidinyl] amino]-5-thiazolecarboxamide, monohydrate compound of formula-1a.

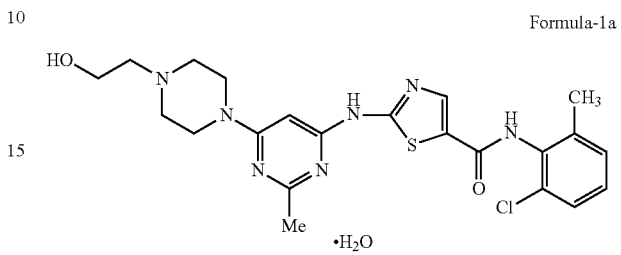

Formula-1a

•H$_2$O

It is a white to off-white powder, insoluble in water and slightly soluble in alcoholic solvents like ethanol and methanol.

U.S. Pat. No. 6,596,746 B1 (herein after. US'746) provided the first disclosure of N-(2-chloro-6-methylphenyl)-2-[[6-[4-(2-hydroxyethyl)-1-piperazinyl]-2-methyl-4-pyrimidinyl]amino]-5-thiazole carboxamide, which also describes the process for preparing Dasatinib.

According to the basic patent US'746, dasatinib is prepared by reaction of the key intermediate of formula-2 with 1-(2-hydroxyethyl)piperazine in the presence of a base and a suitable solvent. A similar preparation method was later used in a number of other process patents, only varying the corresponding base or solvent. Through the selection of a suitable solvent or procedure a great number of solvates or polymorphs can be prepared. Polymorphs have been one of the most frequently studied physical characteristics of active pharmaceutical substances (API) recently. Thus, different polymorphs of one API may have entirely different physical-chemical properties such as solubility, melting point, mechanical resistance of crystals but they may also influence the chemical and physical stability. Then, these properties may have an impact on further processes such as handling of the particular API, grinding or formulation method. These various physical-chemical characteristics of polymorphs influence the resulting bioavailability of the solid dosage form. Therefore, looking for new polymorphs and solvates is becoming an important tool for obtaining a polymorph form with the desired physical-chemical characteristics.

U.S. Pat. No. 7,491,725 B2 (herein after US'725) describes the crystalline monohydrate, crystalline butanol solvate, crystalline ethanol solvate and anhydrous forms of Dasatinib (i.e., N-6 and T1H1-7). US '725 B2 also provides processes for the preparation of these mentioned forms of Dasatinib. Its continuation U.S. Pat. No. 8,242,270B2 also describes two ethanol solvates, i.e., hemi-ethanol and diethanol solvates.

PCT International Publication No WO2009053854A2 describes the preparation of a number of solvates or mixed solvates out of which especially the isopropanol, and mixed isopropanol/dimethyl sulfoxide solvates, as well as a new solid form B, another anhydrous polymorph of dasatinib, are worth mentioning.

PCT International Publication No WO2010067374A2 describes the preparation of other solvates/mixed solvates such as dimethyl formamide, isopropyl acetate, toluene, dimethyl sulfoxide and processes for the preparation.

API solvates or salts are used in drug formulations in many cases. In the case of solvates the limits for individual solvents, their contents or maximum daily doses have to be strictly observed. Then, these limits can dramatically restrict their effective use. Thus, the clearly most convenient option is the use of sufficiently stable polymorphs of API that do not contain any solvents bound in the crystalline structure.

Some of the above mentioned patent documents describe preparation of a stable anhydrous form (N-6) of dasatinib.

The discovery of new polymorphic form of a pharmaceutically useful compound provides a new opportunity to improve the performance characteristics of a pharmaceutical product.

The present inventors surprisingly found that the 1,2-propanediol solvate of N-(2-chloro-6-methylphenyl)-2-[[6-[4-(2-hydroxyethyl)-1-piperazinyl]-2-methyl-4-pyrimidinyl]amino]-5-thiazole carboxamide, which is showing advantageous properties such as good solubility.

The present inventors surprisingly found that the stable and pure anhydrous form (N-6) and monohydrate form of N-(2-chloro-6-methylphenyl)-2-[[6-[4-(2-hydroxyethyl)-1-piperazinyl]-2-methyl-4-pyrimidinyl]amino]-5-thiazole carboxamide via 1,2-propanediol solvate of N-(2-chloro-6-methylphenyl)-2-[[6-[4-(2-hydroxyethyl)-1-piperazinyl]-2-methyl-4-pyrimidinyl]amino]-5-thiazole carboxamide, which is showing advantageous properties.

BRIEF DESCRIPTION OF THE INVENTION

The first aspect of the present invention is to provide 1,2-propanediol solvate of N-(2-chloro-6-methylphenyl)-2-[[6-[4-(2-hydroxyethyl)-1-piperazinyl]-2-methyl-4-pyrimidinyl]amino]-5-thiazole carboxamide compound of formula-1b.

The second aspect of the present invention is to provide process for the preparation of 1,2-propanediol solvate of N-(2-chloro-6-methylphenyl)-2-[[6-[4-(2-hydroxyethyl)-1-piperazinyl]-2-methyl-4-pyrimidinyl]amino]-5-thiazole carboxamide compound of formula-1b.

The third aspect of the present invention is to provide an improved process for the preparation of anhydrous crystalline form (N-6) of N-(2-chloro-6-methylphenyl)-2-[[6-[4-(2-hydroxyethyl)-1-piperazinyl]-2-methyl-4-pyrimidinyl]amino]-5-thiazole carboxamide.

The fourth aspect of the present invention is to provide an improved process for the preparation of crystalline N-(2-chloro-6-methylphenyl)-2-[[6-[4-(2-hydroxyethyl)-1-piperazinyl]-2-methyl-4-pyrimidinyl] amino]-5-thiazole carboxamide monohydrate compound of formula-1a.

BRIEF DESCRIPTION OF THE DRAWINGS

FIG. 7: Illustrates the PXRD pattern of N-(2-chloro-6-methyl phenyl)-2-[[6-[4-(2-hydroxyethyl)-1-piperazinyl]-2-methyl-4-pyrimidinyl] amino]-5-thiazole carboxamide monohydrate compound of formula-1a.

FIG. 8: Illustrates the DSC pattern of N-(2-chloro-6-methyl phenyl)-2-[[6-[4-(2-hydroxyethyl)-1-piperazinyl]-2-methyl-4-pyrimidinyl] amino]-5-thiazole carboxamide monohydrate compound of formula-1a.

FIG. 9: Illustrates the Infrared spectrum of N-(2-chloro-6-methyl phenyl)-2-[[6-[4-(2-hydroxyethyl)-1-piperazinyl]-2-methyl-4-pyrimidinyl] amino]-5-thiazole carboxamide monohydrate compound of formula-1a.

DETAILED DESCRIPTION OF THE INVENTION

Figure 1:
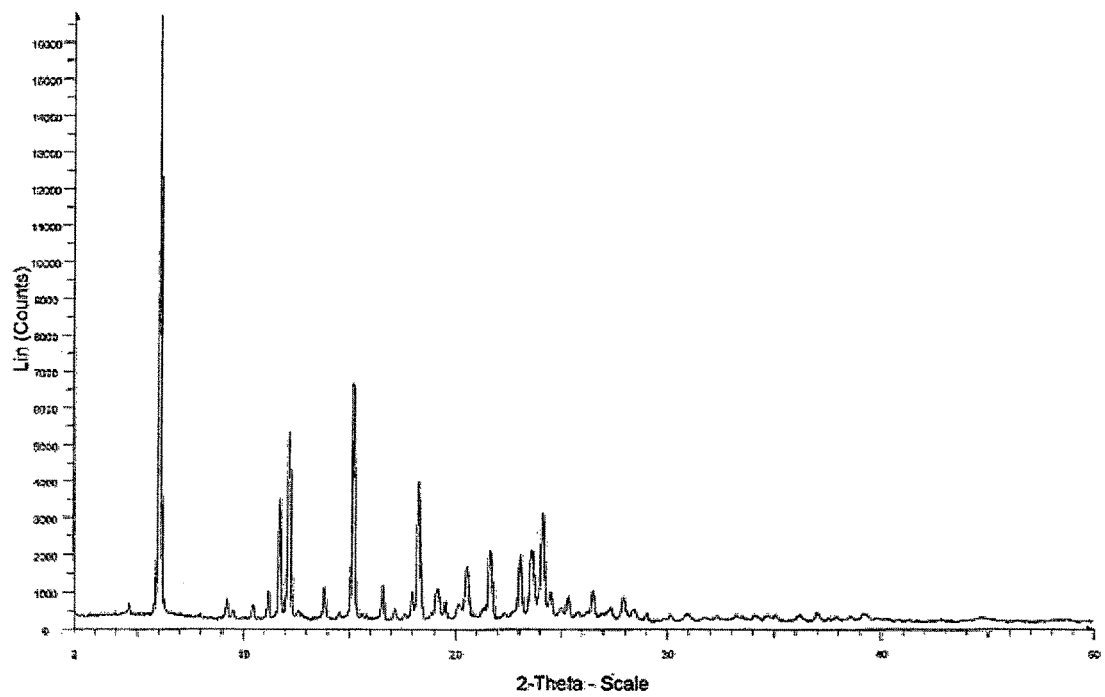
FIG. 1: Illustrates the PXRD pattern of 1,2-propanediol solvate of N-(2-chloro-6-methyl phenyl)-2-[[6-[4-(2-hydroxyethyl)-1-piperazinyl]-2-methyl-4-pyrimidinyl] amino]-5-thiazole carboxamide compound of formula-1b obtained according to example-4.

As used herein the term "suitable solvent" used in the present invention refers to "hydrocarbon solvents" such as n-hexane, n-heptane, cyclohexane, pet ether, benzene, toluene, pentane, cycloheptane, methyl cyclohexane, ethylbenzene, m-, o-, or p-xylene, or naphthalene and the like; "ether solvents" such as dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, 1,2-dimethoxy ethane and the like; "ester solvents" such as methyl acetate, ethyl acetate, isopropyl acetate, n-butyl acetate and the like; "polar-aprotic solvents such as dimethylacetamide (DMA), dimethylformamide (DMF), dimethylsulfoxide (DMSO), N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutylketone and the like; "nitrile solvents" such as acetonitrile, propionitrile, isobutyronitrile and the like; "alcoholic solvents" such as methanol, ethanol, n-propanol, isopropanol, n-butanol, isobutanol, t-butanol, 2-nitroethanol, 2-fluoroethanol, 2,2,2-trifluoroethanol, ethylene glycol, 1,2-propanediol (propylene glycol), 2-methoxyethanol, 1, 2-ethoxyethanol, diethylene glycol, 1, 2, or 3-pentanol, neo-pentyl alcohol, t-pentyl alcohol, diethylene glycol monoethyl ether, cyclohexanol, benzyl alcohol, phenol, or glycerol and the like; "polar solvents" such as water or mixtures thereof.

As used herein the present invention the term "suitable base" refers to "alkali metal carbonates" such as sodium carbonate, potassium carbonate, lithium carbonate and the like; "alkali metal bicarbonates" such as sodium bicarbonate, potassium bicarbonate and the like; "alkali metal hydroxides" such as sodium hydroxide, potassium hydroxide, lithium hydroxide and the like; "alkali metal alkoxides" such as sodium methoxide, sodium ethoxide, potassium methoxide, potassium ethoxide, sodium tert.butoxide, potassium tert.butoxide, lithium tert.butoxide and the like; alkali metal hydrides such as sodium hydride, potassium hydride, lithium hydride and the like; alkali metal amides such as sodium amide, potassium amide, lithium amide and the like; and organic bases like dimethylamine, diethylamine, diisopropyl amine, diisopropylethylamine, diisobutylamine, triethylamine, pyridine, 4-dimethylaminopyridine (DMAP), N-methyl morpholine (NMM), 2,6-lutidine, lithium diisopropylamide; organosilicon bases such as lithium hexamethyldisilazide (LiHMDS), sodium hexamethyldisilazide (NaHMDS), potassium hexamethyldisilazide (KHMDS) or mixtures thereof.

The first aspect of the present invention provides 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b.

Figure 6:
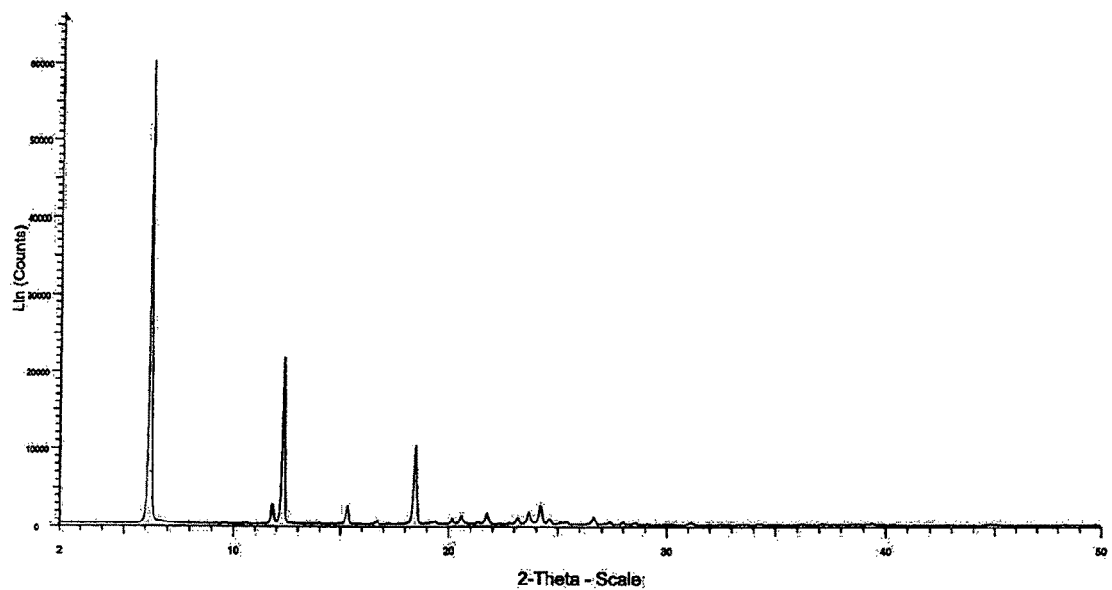
FIG. 6: Illustrates the PXRD pattern of 1,2-propanediol solvate of N-(2-chloro-6-methyl phenyl)-2-[[6-[4-(2-hydroxyethyl)-1-piperazinyl]-2-methyl-4-pyrimidinyl] amino]-5-thiazole carboxamide compound of formula-1b obtained according to example-6.

The 1,2-propanediol solvate of the present invention is characterized by its powder X-Ray diffraction pattern having peaks at about 6.1, 12.2 & 15.2±0.2 degrees of 2-theta. The 1,2-propanediol solvate of the present invention is further characterized by its X-Ray powder diffraction pattern having additional peaks at about 6.1, 11.7, 12.2, 15.2, 16.6, 18.3, 20.4, 21.6, 23.1, 23.6, 24.1, 24.5, 26.6, 31.1±0.2 degrees of 2-theta. The 1,2-propanediol solvate of N-(2-chloro-6-methylphenyl)-2-[[6-[4-(2-hydroxyethyl)-1-piperazinyl]-2-methyl-4-pyrimidinyl]amino]-5-thiazole carboxamide compound of formula-1b is further characterized by the PXRD pattern as illustrated in figure-6.

Figure 3:
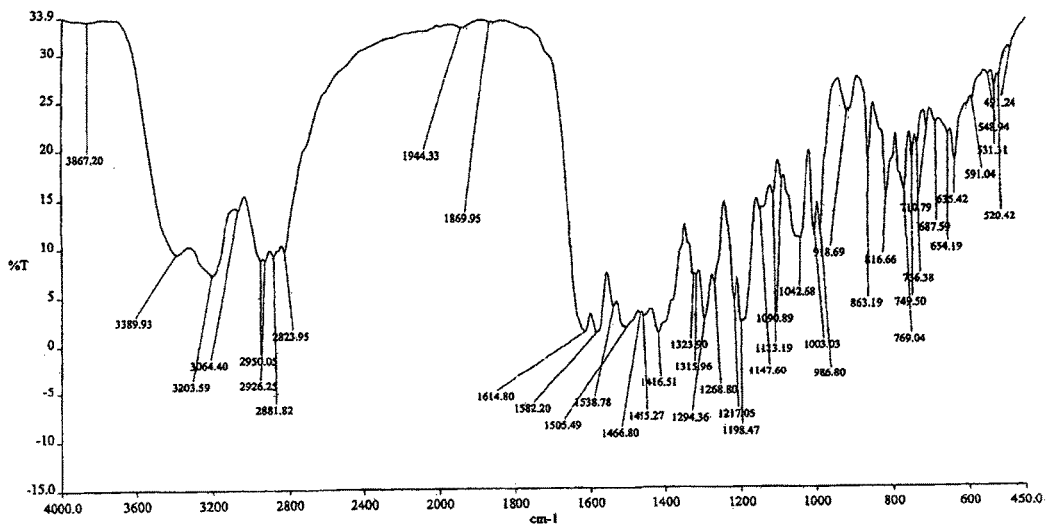
FIG. 3: Illustrates the Infrared spectrum of 1,2-propanediol solvate of N-(2-chloro-6-methyl phenyl)-2-[[6-[4-(2-hydroxyethyl)-1-piperazinyl]-2-methyl-4-pyrimidinyl] amino]-5-thiazole carboxamide compound of formula-1b.

Further, 1,2-propanediol solvate compound of formula-1b is characterized by its differential scanning calorimetric (DSC) thermogram which is showing first endotherm at about 130-185° C., and the second endotherm at about 265-290° C. and the same has been illustrated in figure-3.

Figure 4:
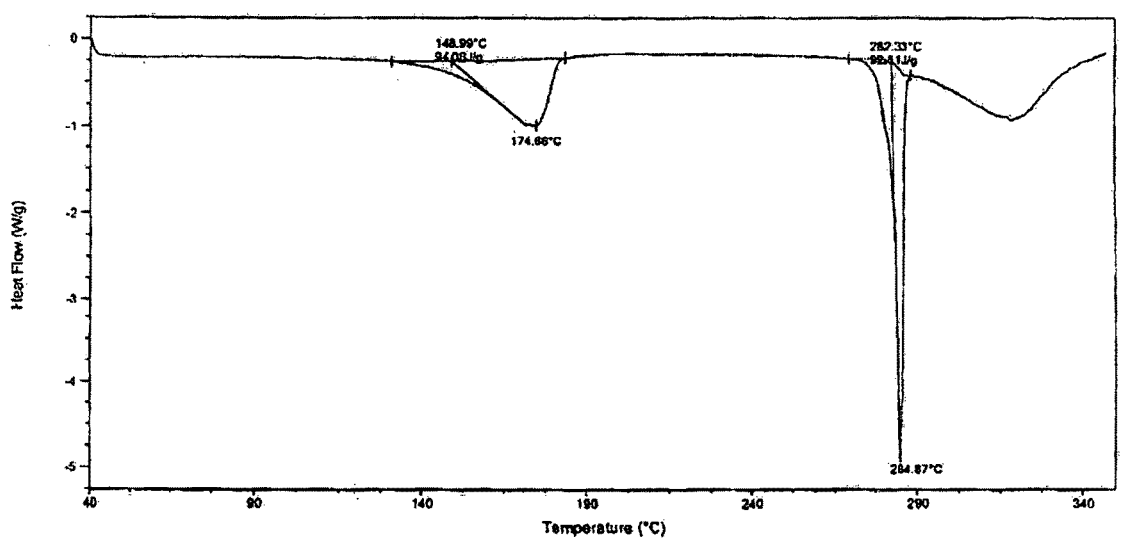
FIG. 4: Illustrates the DSC pattern of 1,2-propanediol solvate of N-(2-chloro-6-methyl phenyl)-2-[[6-[4-(2-hydroxyethyl)-1-piperazinyl]-2-methyl-4-pyrimidinyl] amino]-5-thiazole carboxamide compound of formula-1b.

The 1,2-propanediol solvate of N-(2-chloro-6-methyl phenyl)-2-[[6-[4-(2-hydroxyethyl)-1-piperazinyl]-2-methyl-4-pyrimidinyl] amino]-5-thiazole carboxamide compound of formula-1b is further characterized by its IR absorption spectrum having absorption bands at 3867, 3389, 2881, 1614, 1147, 1198, 1042, 918 cm$^{-1}$ as illustrated in figure-4.

The crystalline 1,2-propanediol solvate of N-(2-chloro-6-methyl phenyl)-2-[[6-[4-(2-hydroxyethyl)-1-piperazinyl]-2-methyl-4-pyrimidinyl] amino]-5-thiazole carboxamide compound of formula-1 obtained according the present invention having 1,2-propanediol content not more than 15%.

It is known in the art that X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realize that the relative intensities of the peaks may vary according to the orientation of the sample under test and on the type and setting of the instrument used. The skilled person will also realize that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a powder diffraction pattern substantially identical to those disclosed herein fall within the scope of the present disclosure.

Generally, a measurement error of a diffraction angle in an X-ray powder diffraction pattern is typically ±0.2° of 2-theta.

The second aspect of the present invention provides a process for the preparation of 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b,

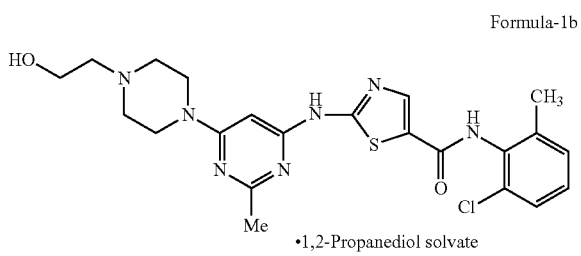 [SMILES: Cc1nc(Nc2ncc(C(=O)Nc3c(C)cccc3Cl)s2)cc(N2CCN(CCO)CC2)n1]

Formula-1b which comprises of:
a) Reacting the 2(6-chloro-2-methylpyrimidin-4-ylamino)-N-(2-chloro-6-methylphenyl) thiazole-5-carboxamide compound of formula-2

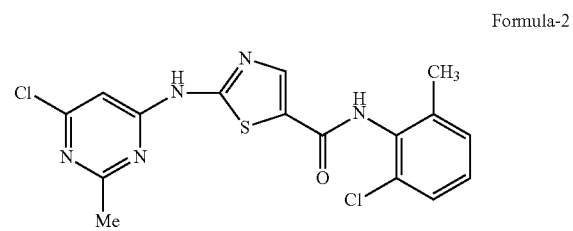 [SMILES: Cc1nc(Cl)cc(Nc2ncc(C(=O)Nc3c(C)cccc3Cl)s2)n1]

Formula-2 with 2-(piperazine-1-yl)ethanol compound of formula-3

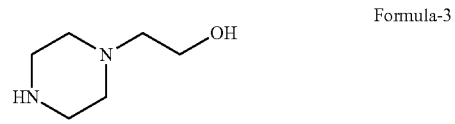

Formula-3 in 1,2-propanediol in presence of a suitable base at a suitable temperature,
b) isolating 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b,
c) optionally purifying the obtained compound in step-b) to get pure compound of formula-1b.

Wherein, in step-a) the suitable base is selected from organic or inorganic base; the suitable temperature refers to 0° C. to reflux temperature of the solvent used, preferably 30° C. to 130° C., most preferably 100° C. to 120° C.

In step-b) the term "isolating" refers to the removal of solvent by filtration or distillation or decantation from the reaction mixture.

The preferred embodiment of the above aspect of the present invention provides a process for the preparation of 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b, which comprises of:
  a) Reacting the 2(6-chloro-2-methylpyrimidin-4-ylamino)-N-(2-chloro-6-methylphenyl)thiazole-5-carboxamide compound of formula-2 with 2-(piperazine-1-yl)ethanol compound of formula-3 in 1,2-propanediol in presence of diisopropyl ethyl amine at temperature about 100-120° C.,
  b) isolating the compound of formula-1b by filtering the reaction mixture,
  c) purifying the obtained compound in step-b) by recrystallization from 1,2-propanediol provides pure 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b.

The third aspect of the present invention provides an improved process for the preparation of anhydrous crystalline form (N-6) of N-(2-chloro-6-methylphenyl)-2-[[6-[4-(2-hydroxyethyl)-1-piperazinyl]-2-methyl-4-pyrimidinyl] amino]-5-thiazole carboxamide, which comprises of:
  a) Reacting the 2(6-chloro-2-methylpyrimidin-4-ylamino)-N-(2-chloro-6-methyl phenyl)thiazole-5-carboxamide compound of formula-2 with 2-(piperazine-1-yl)ethanol compound of formula-3 in 1,2-propanediol in presence of base at a suitable temperature,
  b) isolating 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b,
  c) dissolving the obtained compound in step-b) in a suitable solvent at a suitable temperature,
  d) cooling the reaction mixture,
  e) filtering the precipitated solid,
  f) drying to get anhydrous crystalline form (N-6) of N-(2-chloro-6-methylphenyl)-2-[[6-[4-(2-hydroxyethyl)-1-piperazinyl]-2-methyl-4-pyrimidinyl]amino]-5-thiazole carboxamide,
  g) optionally purifying the obtained compound in step-f) using a suitable solvent.
  Wherein, in step-a) a suitable base is selected from organic or inorganic base; the suitable temperature refers to about 0° C. to reflux temperature of the solvent used, preferably 30° C. to 130° C., most preferably 100° C. to 120° C.
  In step-b) the term "isolating" refers to the removal of solvent by filtration or distillation or decantation from the reaction mixture.
  In step-c) the suitable temperature refers is selected from 25° C. to reflux temperature of the solvent used, preferably 40° C. to 65° C., most preferably 50° C. to 65° C.
  In step-c) and step-f) the suitable solvent is selected from alcohol solvents, ketone solvents, nitrile solvents, polar solvents, ester solvents and mixtures thereof.

The preferred embodiment of the above aspect of the present invention provides an improved process for the preparation of anhydrous crystalline form (N-6) of N-(2-chloro-6-methylphenyl)-2-[[6-[4-(2-hydroxyethyl)-1-piperazinyl]-2-methyl-4-pyrimidinyl] amino]-5-thiazole carboxamide, which comprises of:
  a) Reacting the 2(6-chloro-2-methylpyrimidin-4-ylamino)-N-(2-chloro-6-methylphenyl) thiazole-5-carboxamide compound of formula-2 with 2-(piperazine-1-yl)ethanol compound of formula-3 in 1,2-propanediol in presence of diisopropyl ethyl amine at temperature about 100-120° C.,
  b) isolating 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b by filtering the reaction mixture,
  c) dissolving the obtained compound in methanol at reflux temperature,
  d) cooling the reaction mixture,
  e) filtering the precipitated solid,
  f) drying to get anhydrous crystalline form (N-6) of N-(2-chloro-6-methylphenyl)-2-[[6-[4-(2-hydroxyethyl)-1-piperazinyl]-2-methyl-4-pyrimidinyl]amino]-5-thiazole carboxamide, The 2(6-chloro-2-methylpyrimidin-4-ylamino)-N-(2-chloro-6-methylphenyl) thiazole-5-carboxamide compound of formula-2 is prepared by the process known in the art.

Further aspect of the present invention provides an improved process for the preparation of anhydrous crystalline form (N-6) of N-(2-chloro-6-methylphenyl)-2-[[6-[4-(2-hydroxyethyl)-1-piperazinyl]-2-methyl-4-pyrimidinyl] amino]-5-thiazole carboxamide, which comprises of:
  a) Reacting the 2(6-chloro-2-methylpyrimidin-4-ylamino)-N-(2-chloro-6-methyl phenyl)thiazole-5-carboxamide compound of formula-2 with 2-(piperazine-1-yl)ethanol compound of formula-3 in 1,2-propanediol in presence of a base at a suitable temperature,
  b) isolating 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b,
  c) dissolving the compound obtained in step-b) in a suitable solvent at a suitable temperature,
  d) cooling the reaction mixture,
  e) adding a suitable solvent to the above reaction mixture,
  f) filtering the precipitated solid,
  g) drying to get anhydrous crystalline form (N-6) of N-(2-chloro-6-methylphenyl)-2-[[6-[4-(2-hydroxyethyl)-1-piperazinyl]-2-methyl-4-pyrimidinyl] amino]-5-thiazole carboxamide,
  h) optionally purifying the obtained compound in step-g) using a suitable solvent.
  Wherein, in step-a) the suitable base is selected from organic or inorganic base; the suitable temperature refers to about 0° C. to reflux temperature of the solvent used, preferably 30° C. to 130° C., most preferably 100° C. to 120° C.
  In step-b) the term "isolating" refers to the solvent removed by filtration or distillation or decanted the solvent from the reaction mixture.
  In step-c) the suitable solvent is selected from alcohol solvents, preferably methanol; the suitable temperature refers to about 25° C. to reflux temperature of the solvent used, preferably 40° C. to 65° C., most preferably 50° C. to 65° C.
  In step-e) the suitable solvent is selected from ketone solvents, preferably acetone.
  In step-h) the suitable solvent is selected from alcohol solvents, ketone solvents, nitrile solvents, polar solvents, ester solvents and mixtures thereof.

Preferred embodiment of the present invention provides an improved process for the preparation of anhydrous crystalline form (N-6) of N-(2-chloro-6-methylphenyl)-2-[[6-[4-(2-hydroxyethyl)-1-piperazinyl]-2-methyl-4-pyrimidinyl] amino]-5-thiazole carboxamide, which comprises of:

a) Reacting the 2-(6-chloro-2-methylpyrimidin-4-ylamino)-N-(2-chloro-6-methyl phenyl)thiazole-5-carboxamide compound of formula-2 with 2-(piperazine-1-yl)ethanol compound of formula-3 in 1,2-propanediol in presence of base at 100-120° C.,
b) isolating 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b,
c) dissolving the compound obtained in step-b) in methanol at 50-60° C.,
d) cooling the reaction mixture,
e) adding acetone to the above reaction mixture,
f) filtering the precipitated solid,
g) drying to get anhydrous crystalline form (N-6) of N-(2-chloro-6-methylphenyl)-2-[[6-[4-(2-hydroxyethyl)-1-piperazinyl]-2-methyl-4-pyrimidinyl] amino]-5-thiazole carboxamide.

The fourth aspect of the present invention provides an improved process for the preparation of stable crystalline N-(2-chloro-6-methylphenyl)-2-[[6-[4-(2-hydroxyethyl)-1-piperazinyl]-2-methyl-4-pyrimidinyl] amino]-5-thiazole carboxamide monohydrate of compound of formula-1a, Formula-1a

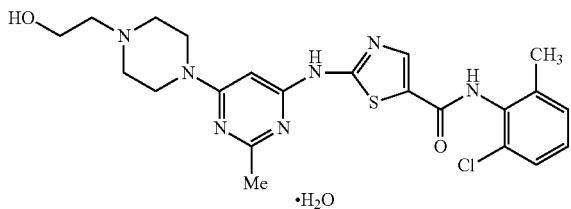

·H₂O comprising of:
a) Reacting the 2-(6-chloro-2-methylpyrimidin-4-ylamino)-N-(2-chloro-6-methyl phenyl)thiazole-5-carboxamide compound of formula-2 with 2-(piperazin-1-yl)ethanol compound of formula-3 in 1,2-propanediol in presence of a suitable base at a suitable temperature to get 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b,
b) optionally purifying the obtained compound in step-a) using 1,2-propanediol,
c) dissolving the compound obtained in step-a) or step-b) in the suitable solvent at the suitable temperature,
d) optionally treating the reaction mixture with carbon,
e) cooling the reaction mixture obtained in step-c) or step-d),
f) filtering the precipitated solid,
g) dissolving the compound obtained in step-f) in the suitable solvent at the suitable temperature,
h) adding water to the reaction mixture obtained in step-g) at the suitable temperature,
i) cooling the reaction mixture,
j) isolating the stable crystalline N-(2-chloro-6-methylphenyl)-2-[[6-[4-(2-hydroxyethyl)-1-piperazinyl]-2-methyl-4-pyrimidinyl] amino]-5-thiazole carboxamide monohydrate of compound of formula-1a.

Wherein,
in step-a) the suitable base is selected from organic or inorganic base; the suitable temperature refers to 0° C. to reflux temperature, preferably 30° C. to 130° C., most preferably 100° C. to 120° C.;
in step-c) and step-g) the suitable solvent is selected from alcohol solvents, chloro solvents, ketone solvents, hydrocarbon solvents, ester solvents, ether solvents, polar solvents, water or mixtures thereof;
in step-c), step-g) and step-h) the suitable temperature refers to about 25° C. to reflux temperature of the reaction mixture,
in step-j) the term "isolating" refers to the solvent removed by filtration or distillation of solvent or decanted the solvent from the reaction mixture.

The preferred embodiment of the above aspect of the present invention provides an improved process for the preparation of stable crystalline N-(2-chloro-6-methylphenyl)-2-[[6-[4-(2-hydroxyethyl)-1-piperazinyl]-2-methyl-4-pyrimidinyl]amino]-5-thiazole carboxamide monohydrate of compound of formula-1a, comprising of:
a) Reacting the 2-(6-chloro-2-methylpyrimidin-4-ylamino)-N-(2-chloro-6-methyl phenyl)thiazole-5-carboxamide compound of formula-2 with 2-(piperazin-1-yl)ethanol compound of formula-3 in 1,2-propanediol in presence of diisopropyl ethylamine at 110-120° C. to get 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b,
b) dissolving the compound obtained in step-a) in methanol at 60-70° C.,
c) treating the reaction mixture with carbon,
d) cooling the reaction mixture,
e) filtering the precipitated solid,
f) dissolving the compound obtained in step-e) in the mixture of water and methanol at 60-70° C.,
g) adding water to the reaction mixture obtained in step-f) at 60-70° C.,
h) cooling the reaction mixture,
i) filtering the obtained solid to get stable crystalline N-(2-chloro-6-methylphenyl)-2-[[6-[4-(2-hydroxyethyl)-1-piperazinyl]-2-methyl-4-pyrimidinyl] amino]-5-thiazole carboxamide monohydrate of compound of formula-1a.

As used herein the term "pure" referred as HPLC by purity of the compound >95%, preferable >99%, more preferably >99.5%. 1,2-propanediol solvate of N-(2-chloro-6-methyl phenyl)-2-[[6-[4-(2-hydroxyethyl)-1-piperazinyl]-2-methyl-4-pyrimidinyl] amino]-5-thiazole carboxamide compound of formula-1b obtained by the present invention is having purity about 99% by HPLC. Even though the process of the present invention is not proceeding through chromatographic purification, controls all the impurities to below ICH limits in which few of them are controlled to not detected level.

The following impurities are found by the inventors of the present invention during the processes for the preparation of anhydrous crystalline form (N-6), monohydrate and 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide.

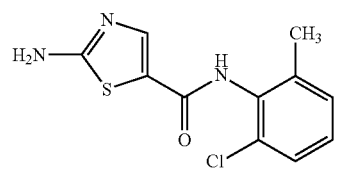

2-amino-N-(2-chloro-6-methylphenyl)thiazole-5-carboxamide [Formula-10]

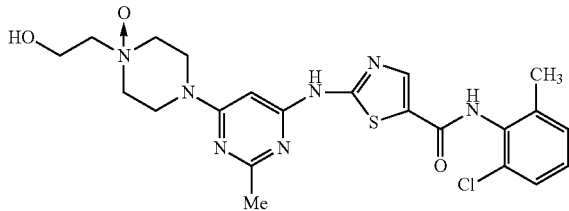 [SMILES: Cc1nc(Nc2ncc(C(=O)Nc3c(C)cccc3Cl)s2)cc(N2CC[N+]([O-])(CCO)CC2)n1]

N-(2-chloro-6-methylphenyl)-2-[[6-[4-(2-hydroxyethyl)-1-piperazinyl]-2-methyl-4-pyrimidinyl]amino-5-thiazole carboxamide N-Oxide [N-Oxide impurity]

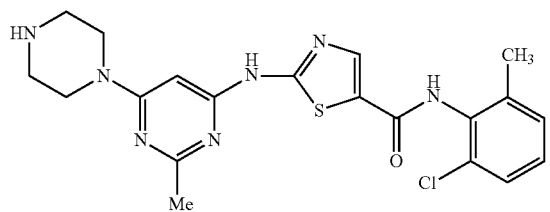 [SMILES: Cc1nc(Nc2ncc(C(=O)Nc3c(C)cccc3Cl)s2)cc(N2CCNCC2)n1]

N-(2-chloro-6-methylphenyl)-2-(2-methyl-6-(piperazin-1-yl)pyrimidin-4-ylamino)thiazole-5-carboxamide [N-Deshydroxy ethyl dasatinib]

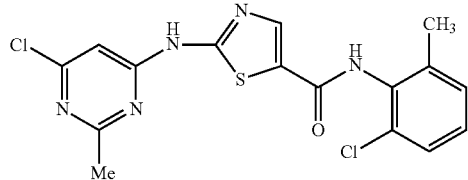 [SMILES: Cc1nc(Cl)cc(Nc2ncc(C(=O)Nc3c(C)cccc3Cl)s2)n1]

2-(6-chloro-2-methylpyrimidin-4-ylamino)-N-(2-chloro-6-methylphenyl)thiazole-5-carboxamide [Formula-2]

HPLC Method of Analysis:
Dasatinib and its related substances were analyzed by HPLC with the following chromatographic conditions:
Apparatus: A liquid chromatograph is equipped with variable wavelength UV Detector. Column: Kromasil 5-C18, 125×4.0 mm, 5 µm (or) Equivalent; Wavelength: 310 nm; Column temperature: 25° C.; Injection volume: 10 µL; Elution: Gradient; Mobile phase-A: Buffer (100%); Mobile phase-B: Acetonitrile: Water (90:10) v/v; Diluent: N,N-Dimethyl formamide; Needle wash: Acetonitrile: Water (50:50) v/v.
Buffer Preparation: Weigh accurately about 3.85 g of Ammonium acetate in 1000 mL of milli-Q water and filter this solution through 0.45 µm nylon membrane filter paper.
N-(2-chloro-6-methyl phenyl)-2-[[6-[4-(2-hydroxyethyl)-1-piperazinyl]-2-methyl-4-pyrimidinyl] amino]-5-thiazole carboxamide, its polymorphs or solvates produced by the present invention can be further micronized or milled to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.
1,2-propanediol solvate, anhydrous crystalline form (N-6) and monohydrate of N-(2-chloro-6-methylphenyl)-2-[[6-[4-(2-hydroxyethyl)-1-piperazinyl]-2-methyl-4-pyrimidinyl] amino]-5-thiazole carboxamide obtained according to the present invention having particle size about less than 1000 µm, preferably <500 µm, most preferably <200 µm, more preferably <100 µm.
PXRD analysis of 1,2-propanediol solvate, anhydrous crystalline form (N-6) and monohydrate N-(2-chloro-6-methylphenyl)-2-[[6-[4-(2-hydroxyethyl)-1-piperazinyl]-2-methyl-4-pyrimidinyl]amino]-5-thiazolecarboxamide were carried out using BRUKER/AXS X-Ray diffractometer using Cu Kα radiation of wavelength 1.5406 A° and continuous scan speed of 0.03°/min.
Differential scanning calorimetric (DSC) analysis was performed on a Q10 V9.6 Build 290 calorimeter with closed aluminium pans, heating the samples from 40 to 350° C. in a dry nitrogen atmosphere at a rate of 10° C./min.
IR spectra were recorded on a Perkin-Elmer FTIR spectrometer.
The present invention represented in the scheme-1.

Scheme-1:

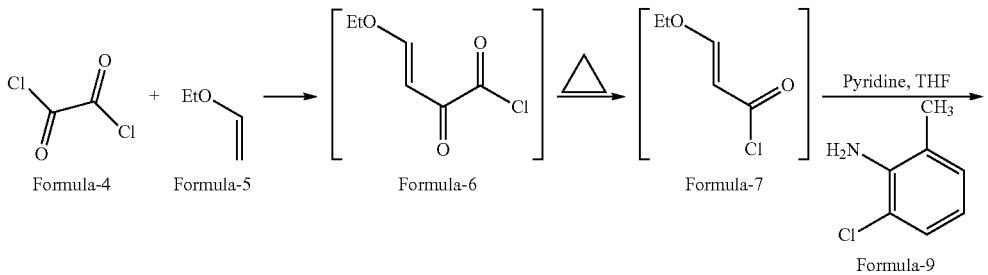

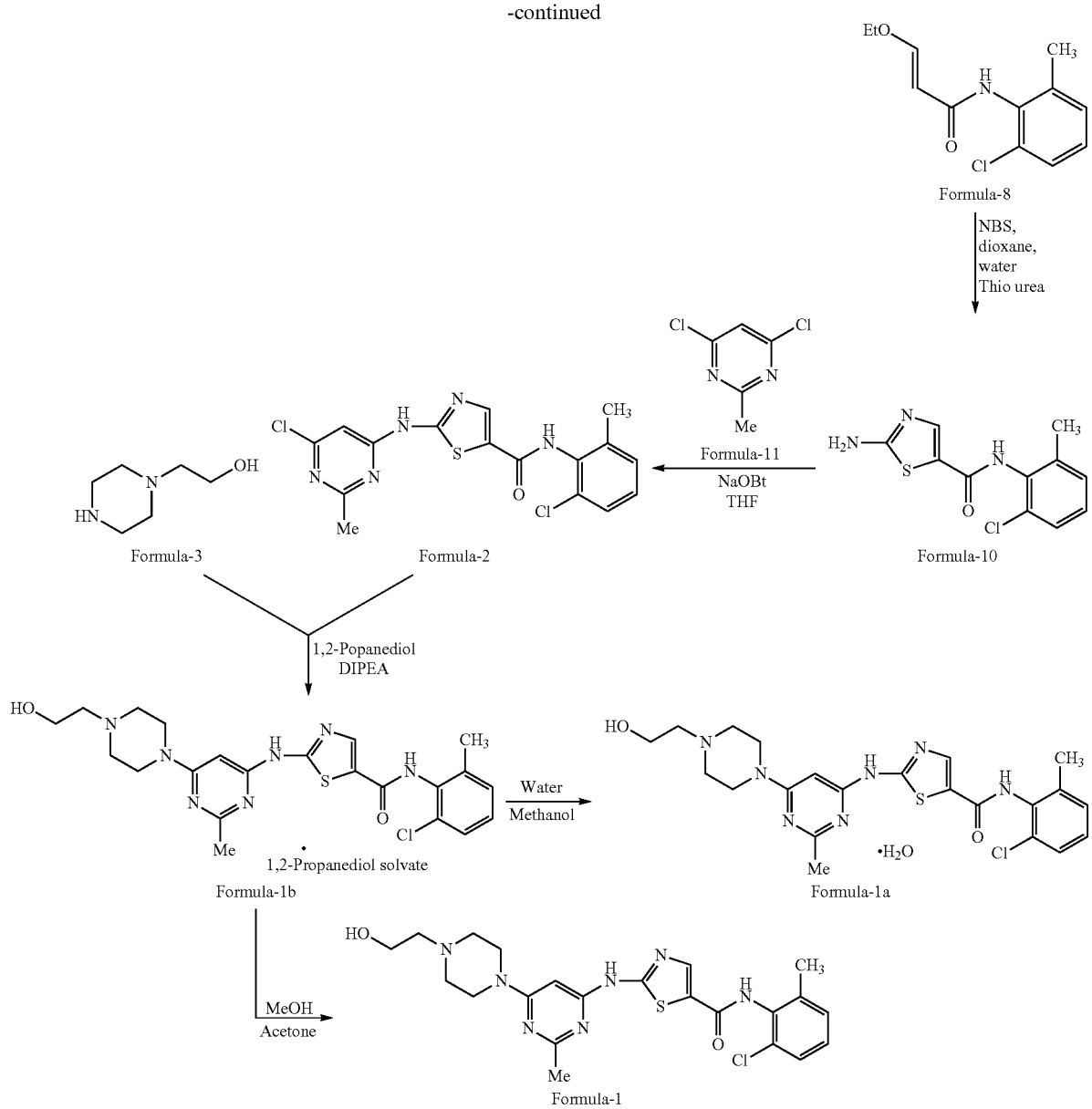

The best mode of carrying out the present invention was illustrated by the below mentioned examples. These examples are provides as illustration only and hence should not be construed as limitation of the scope of the invention.

EXAMPLES

Example-1

Preparation of (E)-N-(2-chloro-6-methylphenyl)-3-ethoxyacrylamide Compound of Formula-8

Ethyl vinyl ether compound of formula-5 (500 gm) was slowly added to oxalyl chloride compound of formula-4 (670 ml) at 10-15° C. Raised the temperature of the reaction mixture to 25-30° C. and stirred for 12 hours at the same temperature. Heated the reaction mixture to 120-125° C. and stirred for 90 minutes at the same temperature. Cooled the reaction mixture to 30-35° C. and (E)-3-ethoxyacryloyl chloride compound of formula-7 was collected by fractional distillation. Added tetrahydrofuran (1160 ml) to the obtained compound of formula-7 and cooled the reaction mixture to 10-15° C. Slowly added a solution of 2-methyl-6-chloroaniline compound of formula-9 (290 gm), pyridine (248 ml) & tetrahydrofuran (1160 ml) to the reaction mixture at same temperature. Raised the temperature of the reaction mixture to 25-30° C. and stirred the reaction mixture for 4 hours at the same temperature. Cooled the reaction mixture to 5-10° C. and acidified the reaction mixture using aqueous HCl solution. Water and ethyl acetate were added to the reaction mixture and stirred for 10 minutes. Separated the both aqueous & organic layers and extracted the aqueous layer with ethyl acetate. Washed the total organic layer with aqueous sodium bicarbonate solution followed by with water. Distilled off the solvent completely from the organic layer under reduced pressure. Ethyl acetate was added to the obtained compound at 25-30° C. and cooled the reaction mixture to 0-5° C. Stirred the reaction mixture for 2 hours at the same temperature. Filtered the precipitated solid, washed with chilled ethyl acetate and dried the material to get the title compound.

Yield: 300 gm; M.R.: 160-164° C.; HPLC Purity: 99.66%.

Example-2

Preparation of 2-Amino-N-(2-chloro-6-methylphenyl)thiazole-5-carboxamide
Compound of Formula-10

(E)-N-(2-chloro-6-methylphenyl)-3-ethoxyacrylamide compound of formula-8 (240 gm) was added to a mixture of N-bromosuccinimide (267.1 gm), water (960 ml) and 1,4-dioxane (480 ml) at 25-30° C. and stirred the reaction mixture for 3 hours at the same temperature. Thiourea (76.8 gm) was added to the reaction mixture at 25-30° C. Heated the reaction mixture to 65-70° C. and stirred for 2 hours at the same temperature. Cooled the reaction mixture to 15-20° C. The reaction mixture was added slowly to a pre-cooled (15-20° C.) aqueous ammonia solution (600 ml of ammonia in 960 ml of water) at 15-20° C. and stirred the reaction mixture for 2 hours at same temperature. Filtered the precipitated solid and washed with water. Water was added to the obtained compound and stirred for 40 minutes at 25-30° C. Filtered the precipitated solid, washed with water and dried to get the title compound.

Yield: 213 gm; M.R.: 195-200° C.; HPLC Purity: 98.77%.

Example-3

Preparation of 2-(6-chloro-2-methylpyrimidin-4-ylamino)-N-(2-chloro-6-methylphenyl)thiazole-5-carboxamide Compound of Formula-2

A mixture of 2-Amino-N-(2-chloro-6-methylphenyl) thiazole-5-carboxamide (200 gm), tetrahydrofuran compound of formula-10 (1000 ml) & 4,6-dichloro-2-methylpyrimidine compound of formula-11 (159 gm) was cooled to 5-10° C. Freshly prepared solution of sodium tertiary butoxide (251 gm) in tetrahydrofuran (1000 ml) was added to the above reaction mixture at 5-10° C. Raised the temperature of the reaction to 25-30° C. and stirred the reaction mixture for 8 hours at the same temperature. Cooled the reaction mixture to 5-10° C. and water was added to it at the same temperature. Acidified the reaction mixture with aqueous HCl solution at 5-10° C. Raised the temperature of the reaction mixture to 25-30° C. and stirred for 2 hours at the same temperature. Filtered the precipitated solid, washed with water and dried to get the title compound.

Yield: 190 gm; HPLC Purity: 98.52%.

Example-4

Preparation of 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide Compound of Formula-1b A mixture of 2-(6-chloro-2-methylpyrimidin-4-ylamino)-N-(2-chloro-6-methyl phenyl) thiazole-5-carboxamide compound of formula-2 (75 gm), 2-(piperazin-1-yl)ethanol compound of formula-3 (124 gm) & 1,2-propanediol (1125 ml) is expelled with nitrogen for 30 minutes. N,N-diisopropylethylamine (65.4 ml) was added to the reaction mixture and heated the reaction mixture to 115-120° C. Stirred the reaction mixture for 8 hours at the same temperature. Cooled the reaction mixture to 25-30° C. and stirred for 6 hours at the same temperature. Filtered the precipitated solid and washed with 1,2-propanediol. 1,2-propanediol (1575 ml) was added to the obtained wet compound and heated the reaction mixture to 115-120° C. Stirred the reaction mixture for 2 hours at the same temperature. Filtered the reaction mixture at 115-120° C. and washed with 1,2-propanediol. Cooled the filtrate to 25-30° C. and stirred for 2 hours at the same temperature. Filtered the precipitated solid, washed with 1,2-propanediol and dried to get pure 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide.

Yield: 58 gm; HPLC Purity: 99.86%, 0.08% (Formula-5), 0.02% (N-Oxide impurity), 0.025% (Deshydroxyethyl dasatinib);

The PXRD pattern of the obtained compound is depicted in Figure-1.

Example-5

Purification of the Compound of Formula-1b

Dissolved 1,2-propanediol solvate of N-(2-chloro-6-methylphenyl)-2-[[6-[4-(2-hydroxy ethyl)-1-piperazinyl]-2-methyl-4-pyrimidinyl] amino]-5-thiazole carboxamide compound of formula-1b (75 gm) in 1,2-propanediol (1575 ml) at 115-120° C. Stirred the reaction mixture for 2 hours at the same temperature. Filtered the reaction mixture at 115-120° C. and washed with 1,2-propanediol. Cooled the filtrate to 25-30° C. and stirred for 2 hours at the same temperature. Filtered the precipitated solid, washed with 1,2-propanediol and dried to get pure title compound.

Figure 2:
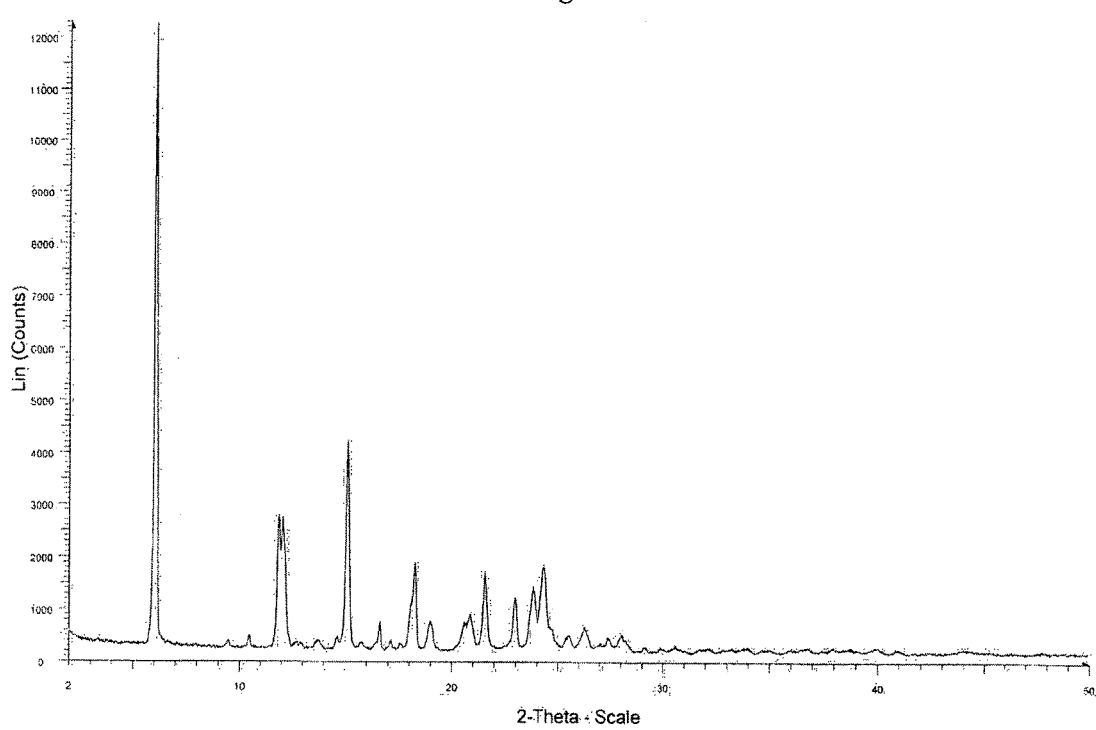
FIG. 2: Illustrates the PXRD pattern of 1,2-propanediol solvate of N-(2-chloro-6-methyl phenyl)-2-[[6-[4-(2-hydroxyethyl)-1-piperazinyl]-2-methyl-4-pyrimidinyl] amino]-5-thiazole carboxamide compound of formula-1b obtained according to example-5.

Yield: 58 gm; HPLC Purity: 99.93%, 0.03% (Formula-5), 0.01% (N-Oxide impurity), 0.02% (Deshydroxyethyl dasatinib);

Particle size: D(10):7.82 µm, D(50): 25.56 µm, D(90): 50.54 µm; PXRD pattern of the obtained compound is depicted in Figure-2.

Example-6

Preparation of 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide Compound of Formula-1b A mixture of 2-(6-chloro-2-methylpyrimidin-4-ylamino)-N-(2-chloro-6-methyl phenyl) thiazole-5-carboxamide compound of formula-2 (25 kg), 2-(piperazin-1-yl)ethanol compound of formula-3 (41.74 kg) & 1,2-propanediol (37.5 lit) is expelled with nitrogen for 30 minutes. N,N-diisopropylethylamine (21.8 lit) was added to the reaction mixture and heated the reaction mixture to 115-120° C. Stirred the reaction mixture for 14 hours at the same temperature. Cooled the reaction mixture to 25-30° C. and stirred for 6 hours at the same temperature. Filtered the precipitated solid and washed with 1,2-propanediol. 1,2-propanediol (1000 lit) was added to the obtained wet compound and heated the reaction mixture to 95-100° C. Stirred the reaction mixture for 40 minutes at the same temperature. Filtered the reaction mixture at 95-100° C. and washed with 1,2-propanediol. Cooled the filtrate to 75-80° C., seeding the filtrate with the compound of formula-1b and stirred for 1 hour at the same temperature. Slowly cooled the reaction mixture to 65-70°

C. and stirred for 1 hour at the same temperature. Slowly cooled the reaction mixture to 55-60° C. and stirred for 1 hour at the same temperature. Slowly cooled the reaction mixture to 45-50° C. and stirred for 1 hour at the same temperature. Slowly cooled the reaction mixture to 30-35° C. Filtered the solid, washed with 1,2-propanediol and dried to get pure 1,2-propanediol solvate of N-(2-chloro-6-methylphenyl)-2-[[6-[4-(2-hydroxyethyl)-1-piperazinyl]-2-methyl-4-pyrimidinyl]amino]-5-thiazole carboxamide.

Yield: 35.77 kg; HPLC Purity: 99.77%, 0.08% (Formula-10), 0.05% (N-Oxide impurity), 0.03% (N-Deshydroxyethyl dasatinib);

Particle size: D(10): 19.716 μm, D(50): 76.576 μm, D(90): 209.359 μm.

PXRD pattern of the obtained compound is depicted in Figure-6.

After micronization of the compound having particle size: D(10): 0.751 μm, D(50): 2.462 μm, D(90): 7.397 μm.

Example-7

Preparation of Anhydrous Crystalline Form (N-6) of N-(2-chloro-6-methylphenyl)-2-[[6-[4-(2-hydroxyethyl)-1-piperazinyl]-2-methyl-4-pyrimidinyl] amino]-5-thiazole carboxamide A mixture of 2-(6-chloro-2-methylpyrimidin-4-ylamino)-N-(2-chloro-6-methyl phenyl) thiazole-5-carboxamide compound of formula-2 (50 gm), 2-(piperazin-1-yl)ethanol compound of formula-3 (82.5 gm) & 1,2-propanediol (750 ml) is expelled with nitrogen for 30 minutes. N,N-diisopropylethylamine (43.6 ml) was added to the reaction mixture and heated the reaction mixture to 115-120° C. Stirred the reaction mixture for 8 hours at the same temperature. Cooled the reaction mixture to 25-30° C. and stirred for 6 hours at the same temperature. Filtered the precipitated solid and washed with 1,2-propanediol. Methanol (1300 ml) was added to the obtained wet compound and heated the reaction mixture to 65-70° C. Stirred the reaction mixture for 2 hours at the same temperature. Filtered the reaction mixture at 65-70° C. and washed with methanol. Cooled the filtrate to 25-30° C. and stirred for 2 hours at the same temperature. Filtered the precipitated solid, washed with methanol and dried to get the title compound.

Figure 5:
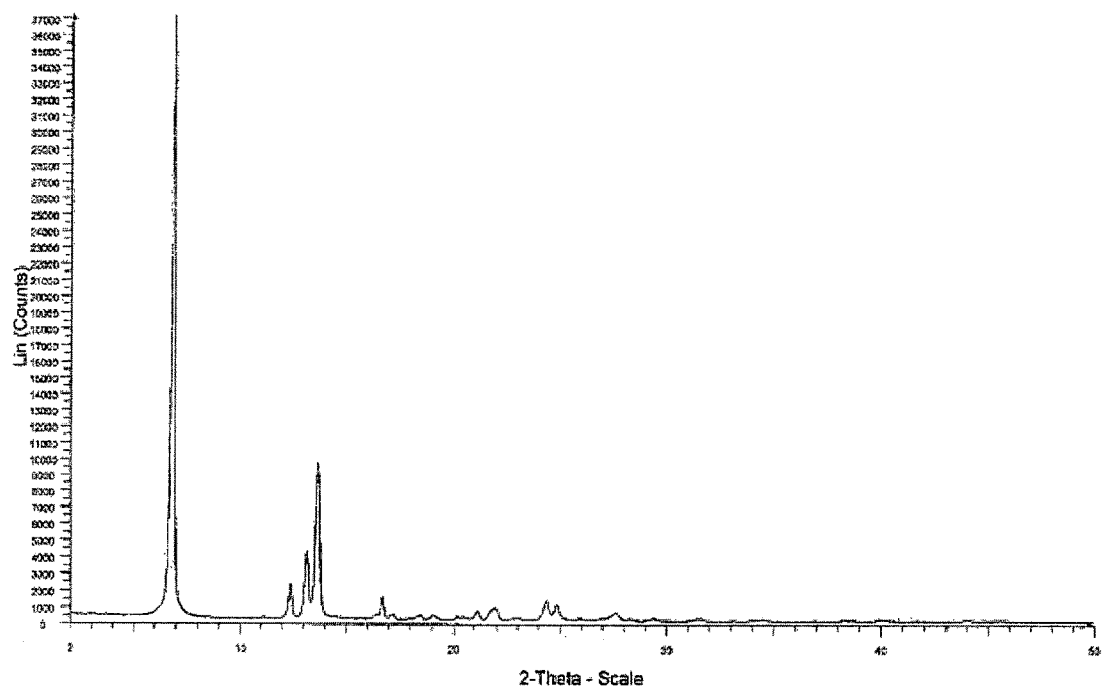
FIG. 5: Illustrates the PXRD pattern of anhydrous crystalline form (N-6) of N-(2-chloro-6-methyl phenyl)-2-[[6-[4-(2-hydroxyethyl)-1-piperazinyl]-2-methyl-4-pyrimidinyl] amino]-5-thiazole carboxamide.

Yield: 38 μm; HPLC Purity: 99.57%, 0.01% (N-Oxide impurity), 0.09% (Deshydroxyethyl dasatinib);

PXRD pattern of the obtained compound depicted in figure-5.

Example-8

Preparation of Anhydrous Crystalline Form (N-6) of N-(2-chloro-6-methylphenyl)-2-[[6-[4-(2-hydroxyethyl)-1-piperazinyl]-2-methyl-4-pyrimidinyl] amino]-5-thiazole carboxamide A mixture of 2-(6-chloro-2-methylpyrimidin-4-ylamino)-N-(2-chloro-6-methyl phenyl) thiazole-5-carboxamide compound of formula-2 (20 kg), 2-(piperazin-1-yl)ethanol compound of formula-3 (33 kg) and 1,2-propanediol (295 lit) is expelled with nitrogen for 30 minutes. N,N-diisopropylethylamine (13 kg) was added to the reaction mixture at 25-30° C. and heated the reaction mixture to 115-120° C. Stirred the reaction mixture for 14 hours at the same temperature. Cooled the reaction mixture to 25-30° C. and stirred for 5 hours at the same temperature. Filtered the precipitated solid and washed with 1,2-propanediol. Dried the material at 70-75° C. for 12 hours. Dissolved the obtained compound in methanol (872 lit) at 55-60° C. Filtered the reaction mixture and washed with methanol. Heated the filtrate to 55-60° C. Cooled the reaction mixture to 25-30° C. and stirred for 2 hours at the same temperature. Acetone (18 lit) was added to the reaction mixture at 25-30° C. and stirred for 3 hours at the same temperature. Filtered the precipitated solid, washed with the mixture of methanol and acetone and dried at 70-80° C. to get the title compound.

Yield: 24.75 kg; HPLC Purity: 99.82%, 0.04% (Formula-10), 0.01% (N-Oxide impurity), 0.06% (N-Des hydroxyethyl dasatinib);

Particle size: D(10): 9.421 μm, D(50): 30.839 μm, D(90): 58.504 μm; PXRD pattern of the obtained compound is depicted in Figure-5.

Example-9

Preparation of crystalline N-(2-chloro-6-methylphenyl)-2-[[6-[4-(2-hydroxyethyl)-1-piperazinyl]-2-methyl-4-pyrimidinyl] amino]-5-thiazole carboxamide monohydrate Compound of Formula-1a A mixture of 2-(6-chloro-2-methylpyrimidin-4-ylamino)-N-(2-chloro-6-methyl phenyl) thiazole-5-carboxamide compound of formula-2 (100 gm), 2-(piperazin-1-yl)ethanol compound of formula-3 (165 gm) & 1,2-propanediol (2250 ml) is expelled with nitrogen for 30 minutes. N,N-diisopropylethylamine (49 ml) was added to the reaction mixture at 25-30° C. and heated the reaction mixture to 115-120° C. Stirred the reaction mixture for 13 hours at the same temperature. Cooled the reaction mixture to 25-30° C. and stirred for 6 hours at the same temperature. Filtered the precipitated solid and washed with 1,2-propanediol. Methanol (4000 ml) was added to the obtained wet compound and heated the reaction mixture to 65-70° C. Stirred the reaction mixture for 60 minutes at the same temperature. Carbon (2 gm) was added to the reaction mixture at 65-70° C. and stirred it for 30 minutes at the same temperature. Filtered the reaction mixture through hyflo bed and washed with methanol. Cooled the obtained filtrate to 25-30° C. and stirred for 2 hours at the same temperature. Filtered the precipitated solid and washed with methanol. Water (300 ml) and methanol (2000 ml) were added to the obtained compound at 25-30° C. Heated the reaction mixture to 65-70° C. and stirred it for 1 hour at the same temperature. Water (800 ml) was slowly added to the reaction mixture at 65-70° C. and cooled the reaction mixture slowly to 0-5° C. Filtered the precipitated solid, washed with the mixture of water and methanol and dried to get the title compound. Yield: 60 μm; water content: 3.68% w/w.

Figure 7:
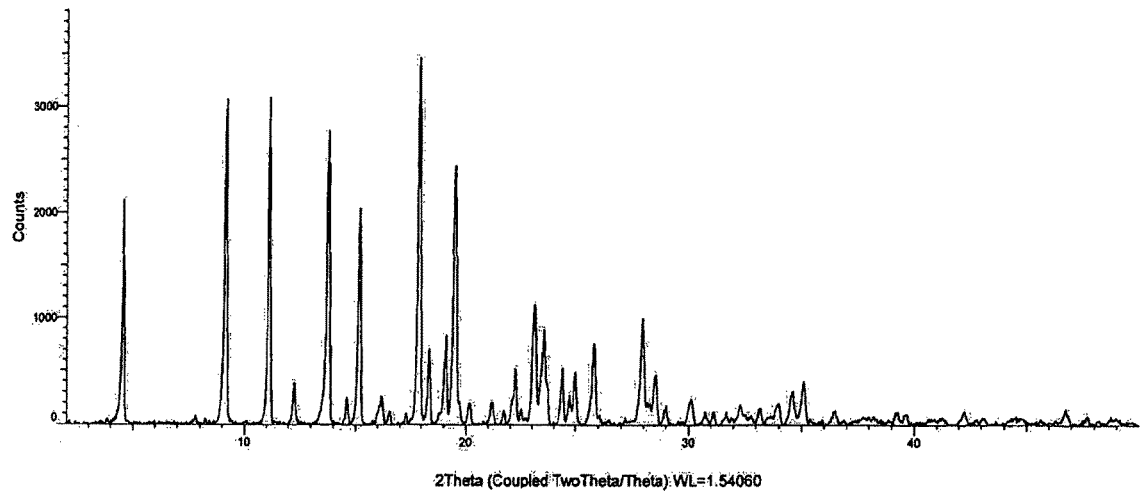
Figure 8:
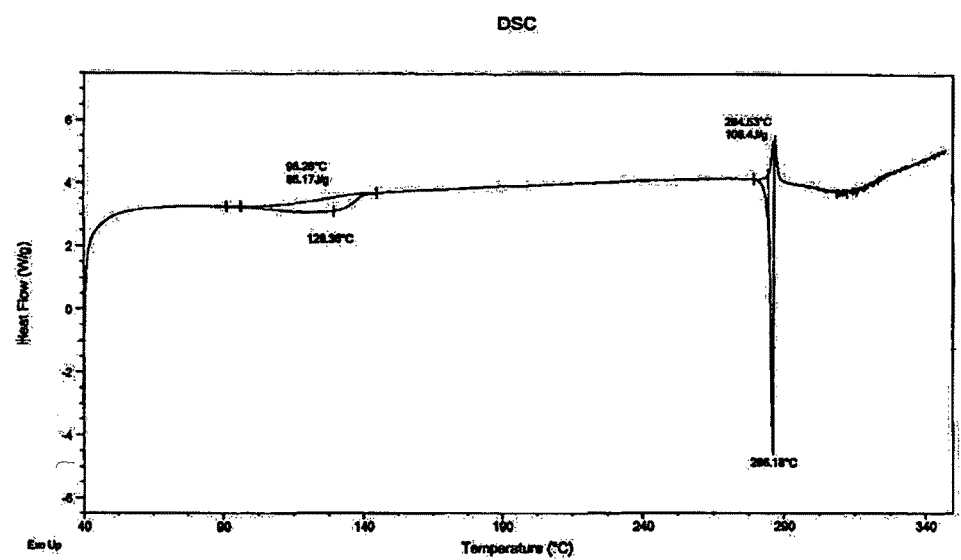
Figure 9:
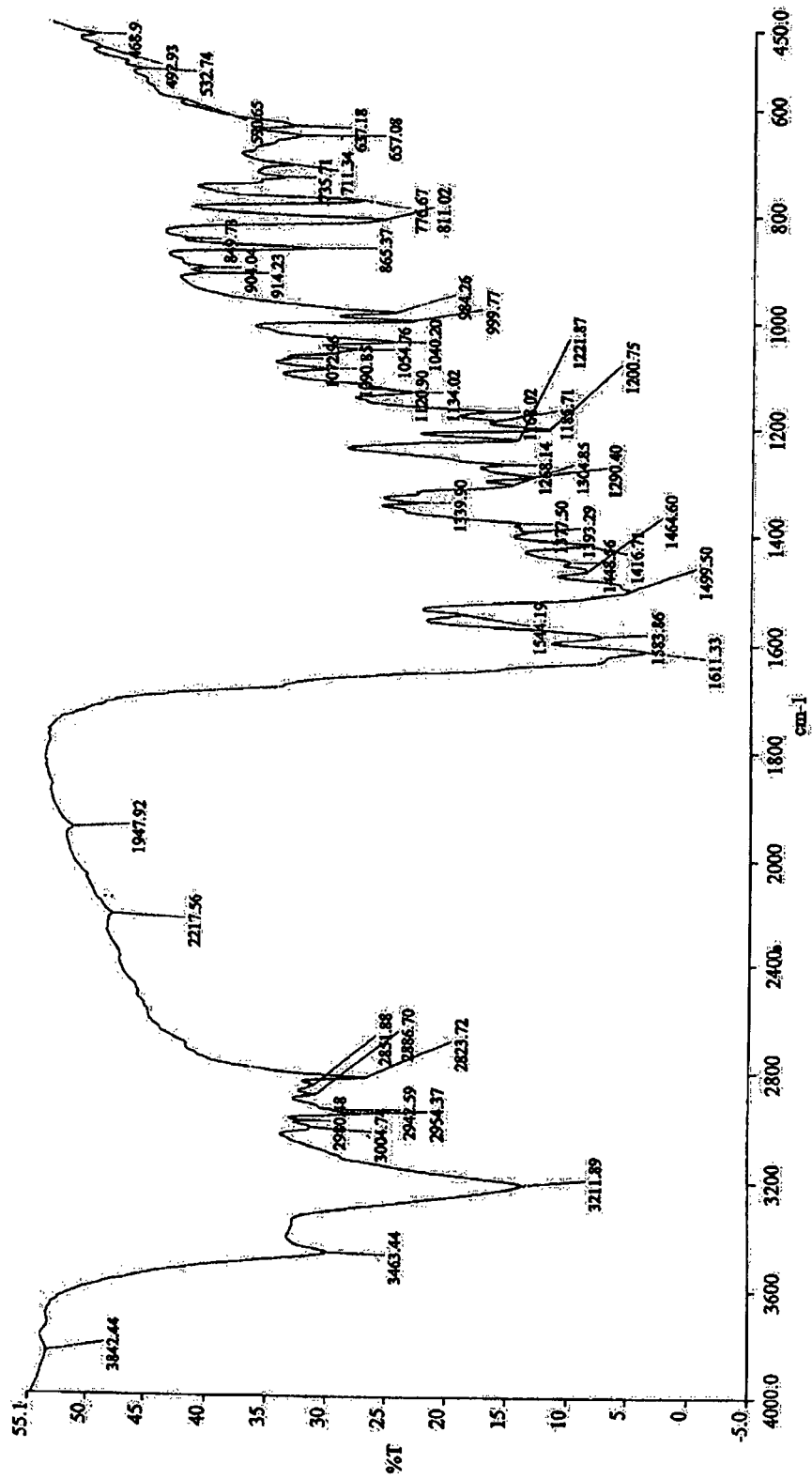

PXRD pattern of the obtained compound is depicted in figure-7.

We claim:
1. A crystalline 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b

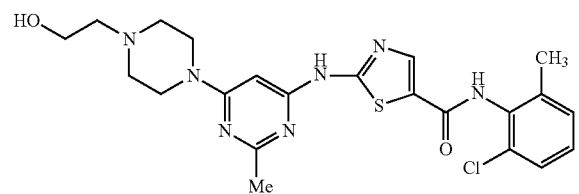

Formula-1b

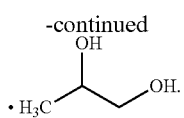

2. The crystalline 1,2-propanediol solvate according to claim 1, characterized by a powder X-Ray diffraction pattern having peaks at about 6.1, 12.2 & 15.2±0.2 degrees of 2-theta.

3. The crystalline 1,2-propanediol solvate according to claim 2, further characterized by an X-Ray diffraction pattern having peaks at about 11.7, 16.6, 18.3, 20.4, 21.6, 23.1, 23.6, 24.1, 24.5, 26.6, 31.1 ±0.2 degrees of 2-theta.

4. The crystalline 1,2-propanediol solvate according to claim 1, having a first endotherm at about 130° C.-185° C., and a second endotherm at about 265-290° C. in its differential scanning calorimetric (DSC) thermogram.

5. The crystalline 1,2-propanediol solvate according to claim 1, having endotherm peaks at about 174° C.±3° C. and 284° C.±3° C. in its differential scanning calorimetric (DSC) thermogram.

6. The crystalline 1,2-propanediol solvate according to claim 1, characterized by absorption peaks at about 3867, 3389, 2881, 1614, 1147, 1198, 1042 and 918±5 cm$^{-1}$ in an infrared spectrum in KBr disc.

7. The crystalline 1,2-propanediol solvate of N-(2-chloro-6-methylphenyl)-2-[[6-[4-(2-hydroxyethyl)-1-piperazinyl]2-methyl-4-pyrimidinyl] amino]-5-thiazole carboxamide, as claimed in claim 1, prepared by a process comprising:
a) reacting the 2(6-chloro-2-methylpyrimidin-4-ylamino)-N-(2-chloro-6-methylphenyl) thiazole-5-carboxamide compound of formula-2

Formula-2

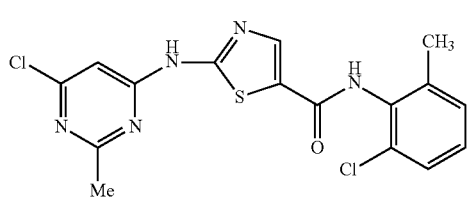

with 2-(piperazine-1-yl)ethanol compound of formula-3

Formula-3

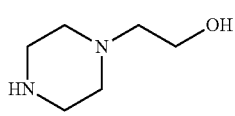

in 1,2-propanediol in presence of a suitable base at a temperature about 100-120° C.,
b) isolating 1,2-propanediol solvate of N-(2-chloro-6-methylphenyl)-2-[[6-[4-(2-hydroxy ethyl)-1-piperazinyl]-2-methyl-4-pyrimidinyl] amino]-5-thiazole carboxamide compound of formula-1b by filtering the reaction mixture,
c) optionally purifying the compound obtained in step-b) using 1,2-propanediol, and
d) optionally drying the obtained compound in step-b) or step-c) to get the 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide.

8. The process for the preparation of crystalline 1,2-propanediol solvate according to claim 7, comprising:
a) reacting the 2(6-chloro-2-methylpyrimidin-4-ylamino)-N-(2-chloro-6-methylphenyl) thiazole-5-carboxamide compound of formula-2 with 2-(piperazine-1-yl)ethanol compound of formula-3 in 1,2-propanediol in presence of diisopropyl ethyl amine at a temperature about 100-120° C., and
b) isolating 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b.

9. A process for the preparation of anhydrous crystalline form (N-6) of N-(2-chloro-6-methylphenyl)-2-[[6-[4-(2-hydroxyethyl)-1-piperazinyl]-2-methyl-4-pyrimidinyl]amino]-5-thiazolecarboxamide, the process comprising:
a) dissolving 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide obtained according to claim 7 in a suitable solvent at a suitable temperature,
b) cooling the reaction mixture,
c) adding the suitable solvent to the reaction mixture, and
d) isolating and drying to get the anhydrous crystalline form (N-6) of N-(2-chloro-6-methylphenyl)-2-[[6-[4-(2-hydroxyethyl)-1-piperazinyl]-2-methyl-4-pyrimidinyl] amino]-5-thiazolecarboxamide.

10. The process according to claim 9, wherein the suitable solvent in step a) is methanol; the suitable temperature in step a) is about 40° C. to reflux temperature of the corresponding solvent; the suitable solvent in step c) is acetone.

11. A process for the preparation of anhydrous crystalline form (N-6) of N-(2-chloro-6-methylphenyl)-2-[[6-[4-(2-hydroxyethyl)-1-piperazinyl]-2-methyl-4-pyrimidinyl]amino]-5-thiazolecarboxamide, the process comprising:
a) dissolving 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide obtained according to claim 7 in a suitable solvent at a suitable temperature,
b) cooling the reaction mixture, and
c) isolating and drying to get the anhydrous crystalline form (N-6) of N-(2-chloro-6-methylphenyl)-2-[[6-[4-(2-hydroxyethyl)-1-piperazinyl]-2-methyl-4-pyrimidinyl] amino]-5-thiazolecarboxamide.

12. The process according to claim 11, wherein the suitable solvent in step a) is methanol; and the suitable temperature in step a) is about 40° C. to reflux temperature of the corresponding solvent.

13. A process for the preparation of crystalline N-(2-chloro-6-methylphenyl)-2-[[6-[4-(2-hydroxyl ethyl)-1-piperazinyl]-2-methyl-4-pyrimidinyl]amino]-5-thiazolecarboxamide monohydrate compound of formula-1a; the process comprising:
a) dissolving 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b obtained according to claim 7 in methanol at a suitable temperature,
b) optionally treating the reaction mixture with carbon,
c) cooling the reaction mixture obtained in step-a) or step-b),
d) filtering the precipitated solid,
e) dissolving the compound obtained in step-d) in the mixture of water and methanol at a suitable temperature,
f) adding water to the reaction mixture obtained in step-e), g) cooling the reaction mixture, and
h) filtering the precipitated solid to get stable crystalline N-(2-chloro-6-methylphenyl)-2-[[6-[4-(2-hydroxyethyl)-1-piperazinyl]-2-methyl-4-pyrimidinyl]amino]-5-thiazole carboxamide monohydrate of compound of formula-1a.

14. The process according to claim 13, wherein the suitable temperature in step a) and step e) is 50-70° C.

15. A process for the preparation of crystalline N-(2-chloro-6-methylphenyl)-2-[[6-[4-(2-hydroxy ethyl)-1-piperazinyl]-2-methyl-4-pyrimidinyl] amino]-5-thiazolecarboxamide monohydrate compound of formula-1a; the process comprising:
    a) dissolving 1,2-propanediol solvate of N-(2-chloro-6-methylphenyl)-2-[[6-[4-(2-hydroxyethyl)-1-piperazinyl]-2-methyl-4-pyrimidinyl] amino]-5-thiazole carboxamide compound of formula-1b obtained according to claim 7 in methanol at 50-70° C.,
    b) optionally treating the reaction mixture with carbon,
    c) cooling the reaction mixture obtained in step-b),
    d) filtering the precipitated solid,
    e) dissolving the compound obtained in step-d) in a mixture of water and methanol at about 60-70° C.,
    f) adding water to the reaction mixture obtained in step-e),
    g) cooling the reaction mixture, and
    h) filtering the obtained solid to get stable crystalline N-(2-chloro-6-methylphenyl)-2-[[6-[4-(2-hydroxyethyl)-1-piperazinyl]-2-methyl-4-pyrimidinyl]amino]-5-thiazole carboxamide monohydrate of compound of formula-1a.

16. The crystalline 1,2-propanediol solvate according to claim 1, having a 1,2-propanediol content of not more than 15%.

17. The crystalline 1,2-propanediol solvate of N-(2-chloro-6-methyl phenyl)-2-[[6-[4-(2-hydroxyethyl)-1-piperazinyl]-2-methyl-4-pyrimidinyl] amino]-5-thiazole carboxamide obtained according to claim 7 having a purity more than 99%.

18. A pharmaceutical composition comprising 1,2-propanediol solvate of N-(2-chloro-6-methyl phenyl)-2-[[6-[4-(2-hydroxyethyl)-1-piperazinyl]-2-methyl-4-pyrimidinyl] amino]-5-thiazole carboxamide obtained according to claim 7, and a pharmaceutically acceptable carrier.

* * * * *